Figure 1:
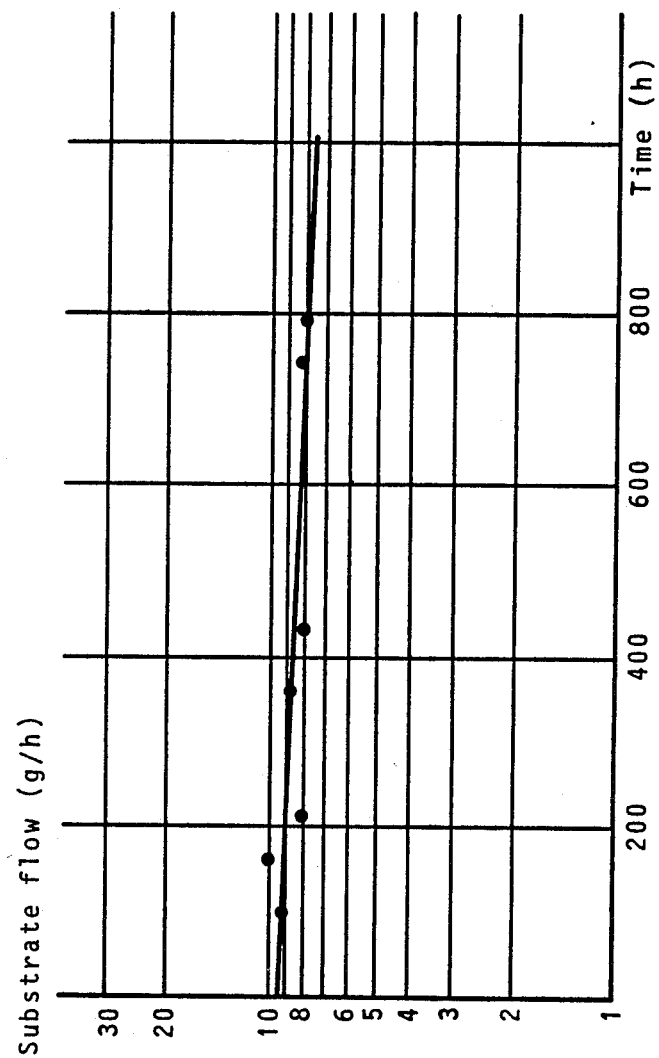

United States Patent [19]

Eigtved

[11] Patent Number: 4,798,793

[45] Date of Patent: Jan. 17, 1989

[54] IMMOBILIZED MUCOR MIEHEI LIPASE FOR TRANSESTERIFICATION

[75] Inventor: Peter Eigtved, Holte, Denmark

[73] Assignee: Novo Industri A/S, Bagsvaerd, Denmark

[21] Appl. No.: 80,214

[22] Filed: Jul. 31, 1987

Related U.S. Application Data

[63] Continuation of Ser. No. 707,792, Mar. 4, 1985, abandoned, which is a continuation-in-part of Ser. No. 646,752, Sep. 5, 1984, abandoned.

[30] Foreign Application Priority Data

Sep. 5, 1983 [DK] Denmark .................. 4025/83

[51] Int. Cl.$^4$ .................. C12P 7/64; C12N 11/08; C12N 9/20; C12R 1/785
[52] U.S. Cl. .................. 435/134; 435/180; 435/198; 435/931
[58] Field of Search ............. 435/134, 180, 198, 931

[56] References Cited

U.S. PATENT DOCUMENTS

| | | | |
|---|---|---|---|
| 4,028,970 | 3/1978 | Fujita et al. .................. | 435/180 |
| 4,065,580 | 12/1977 | Feldman et al. ............... | 435/198 X |
| 4,170,696 | 10/1979 | Hiroharz et al. .............. | 435/180 X |
| 4,263,400 | 4/1981 | Ushiro ........................... | 435/180 X |
| 4,275,081 | 6/1981 | Coleman et al. ............... | 435/134 X |
| 4,472,503 | 9/1984 | Matsuo et al. ................. | 435/180 X |

FOREIGN PATENT DOCUMENTS

| | | | |
|---|---|---|---|
| 37667 | 10/1981 | European Pat. Off. ............ | 435/180 |
| 0069599 | 6/1982 | European Pat. Off. . | |
| 63087 | 4/1982 | Japan ............................ | 435/198 |
| 152886 | 9/1982 | Japan ............................ | 435/180 |

OTHER PUBLICATIONS

J. Lavayre, Biotech. Bioeng., 24, 1007–1013 (1982) Preparation and Properties of Immobilized Lipases.
K. Yokozeki, et al., Enz. Eng., 6, Sep. 20–25, 1981, Ester Exchange of Triglyceride by Entrapped Lipase in Organic Solvent.
K. Yokozeki, et al., Eur. J. Appl. Microbiol. Biotechnol. (1982) 14:1–5.
Y. Kimura et al., Eur. J. Appl. Micro. Bio. (1983) 17:107–112.
Novo Industri, Enzyme Div., No. AF 95.1/3-GB, 8/9/83, Tributyrin pH-stat Method.
Novo Industri, Enzyme Div., No. AF-206/1, 7/5/84, Determination of Lipase Batch.

*Primary Examiner*—David M. Naff
*Attorney, Agent, or Firm*—Morris Fidelman; Franklin D. Wolffe

[57] ABSTRACT

Immobilized lipase is produced by mixing an aqueous lipase solution with a particulate, macroporous, phenol-formaldehyde adsorbent resin, and recovering and drying the resin having lipase immobilized thereon. The resin has a particle size such that more than 90% resin particles have a size between 100–1000 μm. The immobilized lipase is used in a packed bed for continuous transesterfication of solvent free fats. Preferably, the lipase is Mucor miehei lipase. The immobilized lipase has on a dry basis at least 10 batch interesterification units (BIU) and at least 500 lipase units (LU).

9 Claims, 1 Drawing Sheet

IMMOBILIZED MUCOR MIEHEI LIPASE FOR TRANSESTERIFICATION

This application is a continuation of U.S. application, Ser. No. 707,792, filed Sept. 4, 1985, now abandoned, which application was a continuation-in-part of Ser. No. 646,752, filed Sept. 5, 1984, now abandoned.

Immobilized lipase preparations adapted for transesterification or interesterification of fats are known. Thus, in U.S. Pat. No. 4,275,081, immobilized lipase preparations are described whereby the lipase is produced by fermentation of species belonging to the genera Rhizopups, Geotrichum or Aspergillus, and whereby the lipase is attached on an inert particular carrier which may be diatomaceous earth or alumina. These carriers exhibit a very high specific surface area. It was believed necessary to use an immobilized lipase preparation with very high specific surface area (i.e., small and porous carrier particles) in order to obtain high enzymatic activity.

Although interesterification can be carried out batch-wise without a solvent with such immobilized lipase preparations, continuous interesterification in a column cannot be carried out on an industrial scale without the presence of solvent, (which has to be removed later) because the preparation consists of small particles, which during column operation, generate an unacceptably high pressure drop. It is noteworthy that in European Patent Application Publication No. 069599 wherein an enzymatic rearrangement of fat is described with lipase from Aspergillus species, Rhizopus species, *Mucor javanicus* or *Mucor miehei* supported on a carrier, e.g., Celite, all examples relating to continuous interesterification in a column employ a solvent. An immobilized lipase adapted to column operation interesterification of solvent free fats would be welcomed by the art.

The art has, of course, investigated immobilization of numerous enzymes through ionic bonding, covalent binding and entrapment. For example, the inventors of U.S. Pat. No. 4,170,696 note that the controlled size distribution and physical properties of macroporous ion exchange resins offer advantages for enzyme support purposes. These inventors, however, offer objection to the small quantity of enzyme that can be carried per unit weight of the ion exchange resin carrier and suggest employing a diethylaminoethyl (DEAE) derivative of the resins for enzyme support purposes. Teachings such as those posed in U.S. Pat. No. 4,170,696 to the effect that a particular enzyme immobilization technique is broadly applicable to a great many enzyme systems can be criticized for misleading the art. The differences enzyme to enzyme and substrate to substrate make virtually each enzyme/substrate/reaction conditions system an exception to which a technique purported to be broadly applicable will apply poorly, if at all.

Lipases, in particular, are exceptional enzymes in that their enzymatic activity functions at the interface of two liquid phases (water and oil), which alone would indicate that immobilization techniques well suited to other enzymes cannot be expected to apply to lipases well, if at all. The art has recognized that immobilization of lipases present special difficulties. See, for example, J. Lavayre et al., "Preparation and Properties of Immobilized Lipases", Biotechnology and Bioengineering, Vol. XXIV, pp. 1007–1013 (1982), John Wiley & Sons. Some workers in the art, did investigate immobilization of lipase by adsorption or ionic bonding, by covalent binding and by entrapment, concluding that adsorption (on Celite) followed by entrapment of the Celite particles produced by far the best results; see the Poster presented at Enz. Eng. 6, Kashikojima, Japan, Sept. 20–25 1981 and their corresponding Paper in European Journal of Applied Microbiology and biotechnology, No. 14, pp. 1–5 (1982), as well as a successor paper in the same Journal at No. 17, pp. 107–112 (1983).

The prior art referenced hereinabove are but exemplary of the efforts by workers in the art to provide an immobilized lipase suited to facile column operations industrial use. Inasfar as the inventor hereof is aware, the lipase product described in Ser. No. 646,752, of which this application is a continuation-in-part, constitutes a materially superior lipase product for column operations. It is now possible to expand upon the teachings of Ser. No. 646,752 and to describe herein lipase products that are somewhat different from those described previously, yet comparable in their superiority over prior art lipase products.

BRIEF STATEMENT OF THE INVENTION

Now, surprisingly, according to the invention, it has been found that production of an immobilized lipase preparation may be performed very easily by simple mixing of an aqueous solution of lipase and a particulate macroporous phenol-formaldehyde adsorbent resin and thereafter recovering the resin followed by drying. Then, providing a specified proportion of water content in the final immobilized preparation makes possible conduct of continuous interesterification of fats without a solvent, in an economically feasible way. Water washing the resin after removal of the spent lipase solution is advantageous.

In a preferred embodiment of the method according to the invention a thermostable microbial lipase is employed, desirably a lipase from a thermophilic Mucor species, especially *Mucor miehei*. *Mucor miehei* is a good producer of 1,3-specific lipase, and thus a low cost product can be obtained.

In a preferred embodiment of the method according to the invention more than 90% of the particles of the macroporous phenol-formaldehyde adsorbent resin has a particle size between approximately 100 and 1000 $\mu$m, preferably between 400 and 800 $\mu$m. In this particle size interval a good compromise between high unit activity for interesterification and low column pressure drop is obtained.

In a preferred embodiment of the method according to the invention the proportion between the amount of the aqueous solution of the microbial lipase and the weight of the adsorbent resin corresponds to 5,000–50,000 LU/g resin (dry weight). In this interval, sufficient lipase for commercially available resins is provided.

In a preferred embodiment of the method according to the invention when the microbial lipase is derived from a thermophilic Mucor species, especially *Mucor miehei*, the pH during contact between the adsorbent resin and aqueous lipase solution is between 5 and 7. A strong bond between the lipase and the adsorbent resin is secured.

In a preferred embodiment of the method according to the invention, the contact time is between 0.5 and 8 hours. In this time interval saturation of the resin with lipase is approximated. At least 75% of the lipase activity is removed from the lipase solution.

In a preferred embodiment of the method according to the invention, the separation is performed by filtration; a simple procedure well adaptable to industrial practice.

In a preferred embodiment of the method according to the invention, the separated immobilized lipase is dried to a water content between approximately 2 and 40%, more preferably 5–20% of water. Thereby a final lipase preparation with a high interesterification activity is obtained.

DISCUSSION OF THE INVENTION

Thus, the method according to the invention for production of immobilized lipase preparations is as described in Ser. No. 646,752, save for the different resin, namely, an aqueous solution of a microbial lipase is contacted with the particulate macroporous resin, but now with an adsorbent resin of a phenol-formaldehyde matrix. A relatively large average particle size for the resin is employed to make the final product suitable for column operation without excessive pressure drop. The reaction conditions at which the lipase is bonded to the adsorbent resin and the reaction time are sufficient to bind the desired amount of lipase to the adsorbent resin, whereafter the thus formed immobilized lipase is separated from the aqueous phase and the separated lipase containing adsorbent resin is dried to the desired water content, which preferably is between approximately 2 and 20%. The drying operation can be by vacuum, fluid bed drying or any other drying process suited to large scale operation that does not subject the immobilized lipase to temperature levels at which the lipase becomes deactivated.

The term adsorbent resin, as employed herein, has been taken from the ion exchange resin art. The manufacturers of ion exchange resins have found that the particle form resin products into which they had been reacting the active groups that generate the anion or cation exchange activity have commercial utility absent active groups. Such resin forms are offered in commerce as "adsorbent resins". These commercial materials and like others i.e., equivalent in physical and chemical properties are intended herein by the term adsorbent resins. The functional properties of adsorbent resins are mainly due to binding forces other than ionic.

The adsorbent resins known to the inventor hereof are comprised variously of a polystyrene matrix and a phenol-formaldehyde matrix. The practice of this invention is directed to the phenol-formaldehyde class of adsorbent resins. The polystyrene class of adsorbent resins are not contemplated. They are a less advantageous carrier for lipase.

The lipase product of this invention exhibits thermal and physical stability comparable to the products described in Ser. No. 646,752 and may be employed in sustitution therefor.

In order not to inactivate the enzyme, prior art interestification reactions are carried out at the relatively low temperature levels made possible by presence of a solvent capable of dissolving high melting point fats. The immobilized lipase preparations produced according to practice of this invention exhibits sufficient stability in melted fat to catalyze the interesterification at relatively high temperatures. Also, the pressure drop through an interesterification column loaded with the immobilized lipase preparations produced according to practice of this invention is sufficiently low to allow smooth column operation of interesterification reactions. Also, surprisingly, it has been found that the unique combination of contact conditions, adsorbent resin with a phenol-formaldehyde matrix and controlled final water content in the immobilized lipase preparation generates a high specific lipase activity in the melted fat mixture.

The products made according to practice of this invention has been described above in the same laudatory language employed in Ser. No. 646,752, for the products described therein. They are comparable and generally equivalent products, both representing an advance in the art. However, differences exist and such differences may well cause one product mode to become preferred for use in a particular lipase catalyzed process.

The immobilized lipase preparations produced according to practice of this invention can be prepared with a high enzyme recovery, which result is important to attaining a low cost (continuous) interesterification process.

More than 75% of the lipase activity initially present in the lipase solution may be, and should be removed from the solution by the adsorbent resin. To some extent, the lipase take-up by the resin is time dependent, probably because a significant period of time is required for enzyme molecules to diffuse throughout the macroporous resin particles. A mixing (reaction) time of 8 hours will at least approximate equilibrium saturation of the adsorbent resin. Less time, as short as 0.5 hours, produces acceptable results. A reasonable measure for selecting an optimum contact time is removal of lipase activity from the lipase solution. Whatever contact time is required to remove more than 75% of the lipase activity from the lipase solution may become the reaction time for large scale practice of this invention.

It is noted that the available experimental evidence indicates that the optimum contact time will be almost independent of contact temperature, within the range of 5°–35° C., the temperature range of 5°–35° C. is contemplated for practice of this invention.

The physical and chemical differences between various phenol-formaldehyde adsorbent resins can, of course, be expected to affect both the immobilization reaction and the immobilized lipase preparation. As might be expected, all of the experimental work done in genesis of this invention involve commercially available macroporous adsorbent resins, which is to state, that limitations, not known to the inventor hereof, might have been incorporated into the commercial resins. The final immobilized lipase products made according to practice of this invention will exhibit lipase activity with 5,000 to 50,000 LU/gm (dry basis) constituting a preferred range. A unit activity of more than 10 BIU/g can be obtained.

The feature of water washing the still wet resin particles separated from the spent lipase solution is particularly advantageous when the available lipase comprises a relatively crude lipase.

Prior art processes of the sort described in U.S. Pat. No. 4,275,081 have required a purified lipase in order to provide usable immobilized lipase preparations. It has, surprisingly, been found that the immobilized lipase preparations produced according to practice of this invention can be prepared directly from a rather crude lipase product. Apparently, impurities that the prior art wished to remove from the lipase do not bond to the adsorbent resin and then are removed in the spent lipase solution and/or in the wash water.

All in all, highly advantageous results are obtained from a procedure that, in the ultimate, requires nothing more than mixing particulate adsorbent resin into a rather crude lipase solution of pH 5-7 at room temperature, absent even use of an organic solvent (as is sometimes suggested), then discarding the spent solution and then, desirably, water washing the resin followed by drying the resin to a controlled water content. It is repeated that water washing the separated immobilized enzyme before drying significantly improves the product.

It has been found that the lipase in the immobilized lipase preparations produced according to practice of this invention do not deactivate or remove from the preparation readily, absent adverse pH and/or temperature conditions. Almost no lipase activity appears in the wash water, for example.

Mention has been made that preferred embodiments of this invention are directed to immobilizing thermostable lipases, particularly the *Mucor miehei* lipase. Thermal stability for the lipase is, of course, crucial to interesterification of higher melting point fats, absent solvent. Other advantages also accrue when interesterifying at the highest reasonable elevated temperature level, e.g., reduced likelihood for bacterial contamination and lower fat viscosity.

To a great extent, all the many advantages over the prior art described above have virtually no bearing on the practicalities for practice of this invention on a large scale. The same advantages exist for practice of the invention described by the inventor hereof in his parent application, Ser. No. 646,752. That invention might be practiced instead. Decision with regard to large scale practice of this invention can be expected to hinge upon the relative merits thereof compared to preferred modes of practice for the invention of Ser. No. 646,752. Preferred mode process and product circumstances are, therefore, appropriate as realistic, albeit arbitrary, boundary limits to practice of this invention. In specific, removal of lipase activity from the aqueous treatment solution by the adsorbent resin should exceed 75%. The lipase activity unit of the immobilized enzyme product should exceed 5,000 LU/gm (dry basis) (by NOVO method AF 95.1/2-GB). The already mentioned range of 5,000–50,000 LU/gm being preferred. The BIU/g (by NOVO-method AF 206) should exceed 10. The product half life should exceed 2500 hours at 60° C.

The above numerical ranges may serve also to distinguish this invention from practices that expressly are not contemplated by the inventor hereof e.g., employment of polystyrene adsorbent resins, and comparably from expedients that may be derived from the explanation of this invention which follows.

EXPLANATION OF THE INVENTION

Investigation into the mechanism through which the advantageous immobilized lipase products described in Ser. No. 646,752 were generated indicated that not all of their advantageous attributes could be attributed entirely to the weak anion exchange property of the resins on which the lipase is immobilized. The binding capability of the resin for lipase seems to be, in part attributable to anion exchange, in part attributable to other physical forces between lipase and resin, and in part to the chemcial and physical structure of the resin matrix.

Test results from immobilization on three typical commercially available materials exemplify the relationships that are believed to exist.

TABLE 1

| Resin | Type | Matrix | Funct. Groups | Part. Size (um) | Total Capac. (eqv/l) | Immobilized Lipase Yield (%) | Load (LU/mg) | Act. BIU/g |
|---|---|---|---|---|---|---|---|---|
| Duolite ES562 | Weak Base | Phenol Formaldehyde | Tert. Amine | 200-400 | 1.1 | 97 | 25 | 30 |
| Duolite S761 | Almost nonionic | Phenol Formaldehyde | Phenolic | 400-800 | — | 76 | 20 | 20 |
| Duolite S861 | Nonionic | Poly-Styrene | None | 500 | — | 52 | 15 | 4 |

Since multiple relationships are involved, the (arbitrary) multiple criteria for practice of this invention roughly reflect the multiple relationships. Thus, removal of more than 75% of lipase activity from the resin treating solution reflects the overall binding capability of the resin. The minimum unit activity of the immobilized lipase preparation of 5000 LU/gm (dry basis) and of 10 BIU/gm (dry basis) reflects the necessity of a certain minimum loading to obtain activity on a relatively large carried particle.

The cumulative effect of anionic attraction, specific interaction and matrix material in the carrier makes understandable the diversity of prior art suggestions for forming immobilized lipase products (see, for example, U.S. Pat. Nos. 4,275,081; 4,272,503 and 4,451,565, Ex. 12). Apparently a product of sorts will result from immobilization of lipase on virtually any carrier substance. However, the standards set by the parameters of the present invention, namely, 75% yield, 5,000 LU/gm and 10 BIU/g are not believed readily attainable with carriers related to, but outside the scope of this invention, or of its parent application, Ser. No. 646,752. The low yield and activity obtained with a typical polystyrene based adsorbent resin is given in the above Table. In a like test, a strong base polystyrene anion exchange resin (Dowex XY-40008-03) a 12 BIU/g product was obtained, but only 50% yield.

The resins exemplified herein and in parent application, Ser. No. 646,752, have now been discovered to have had pore size and porosity appropriate to practice of this invention. Tests with large pore size anion exchange and adsorbent resins resulted in products of less unit activity than would be predicted from the yield results. It is believed that lipase enters deeply into the pores of very large pore size anion exchange and adsorbent resins, in effect becoming lost therein.

Specific physical interaction and anionic binding appear to be independent sources of binding capability for the resin. The products identified in the above Table 1 were extracted with A: 1% Triton X-100 and C: 1M sodium acetate, pH 6. Conditions A tend to remove only nonionically bound lipase, and Conditions C tend to remove only ionically bound lipase. The results are tabulated below.

TABLE 2

| Resin | Yield (%) | Load (LU/mg) | Activity (BIU/g) | Extraction (% in 1 h., 25° C.) Cycle | A | C |
|---|---|---|---|---|---|---|
| Duolite ES562 w/base ph. | 96 | 25 | 30 | 1. | 0 | 24 |
| | | | | 2. | 0 | 8 |
| Duolite S761 Phenolic | 76 | 20 | 20 | 1. | 39 | 0 |
| | | | | 2. | 10 | 0 |
| Duolite S861 Non-i.ps. | 52 | 15 | 4 | 1. | 29 | 0 |
| | | | | 2. | 7 | 0 |

In sharp contrast to the partial extraction results reported in the above Table 2, lipase adsorbed on Celite was virtually 100% extracted by pure water within a few minutes.

Although the widest process flexibility and/or greatest yield and highest unit activity products obtained by the inventor hereof resulted with weak anion exchange resins, i.e., through practice of Ser. No. 646,752, acceptably high unit activity products in good yield can be obtained with macroporous adsorptive resins of a phenol formaldehyde matrix. An exemplary best mode lipase product on one such adsorbent resin exhibited a half life of more than 3000 hours (the Duolite S761 resin to which allusion has already been made in the above Tables). All things being equal, the inventor hereof would have a modest preference for practice of the invention described in parent application, Ser. No. 646,752, but all things are never equal. Table 2 above demonstrates that substantial product differences exist. The product differences likely will cause products made in accord with practice of this invention to be the more preferred for some lipase catalyzed reactions. Practice of this invention and practice under Ser. No. 646,752 are offered to the art as being closely related inventions of near to equal standing.

DETAILS OF THE INVENTION

The temperature range for conduct of interesterifications according to practice of this invention is 25° C.–85° C., preferably 50° C.–80° C., especially 55° C.–75° C.

Reference is now made to the attached drawing, whereon is plotted important characteristics of a hereinafter exemplified preferred embodiment immobilized lipase for packed bed (column) continuous interesterification, in which:

FIG. 1 shows the logarithm of the flow in g/hr rate plotted against time of hours for a run at 60° C.

The lipase activity unit (LU) indicated in the examples hereinafter provided to describe in detail practice of this invention was determined as described in the publication AF 95.1/2-GB of 83-01-03, obtainable from NOVO INDUSTRI A/S, Novo Alle, 2880 Bagsvaerd, Denmark.

EXAMPLE 1

This Example illustrates the immobilization of lipase according to the invention and characterization of the immobilized enzyme.

Immobilization 1 gram of *Mucor miehei* lipase of 124,000 LU/g was dissolved in 10 ml water and mixed with 4.25 g dry matter of Duolite S-761 resin that had previously been adjusted to pH 6.0 in aqueous suspension (Batch D.E.3.12.7002, Lot 81312E4, 85% of particles 425–825 μm.). pH was then readjusted to 6.0 and the bottle containing the mixture rotated for 2 hours at room temperature during which the pH was readjusted after one hour of rotation.

The resin was filtered, washed twice with 10 ml water, and then dried in vacuum overnight at room temperature.

The combined filtrate of 31 ml and of pH 6.3 contained 700 LU/ml which amounts to about 17.5% of the initial, total enzyme.

The yield of immobilized lipase was 4.91 g at 94.3% dry matter. The calculated load was 22,000 LU/g dry.

Batch Interesterification Activity

This analysis was done according to the internal NOVO method AF 206 described hereinafter. The activity was 20.3 BIU/g.

Test in Column

Precolumn 30 g Duolite A 561, 86% dry matter hydrated with 21 g water is packed in a 2.5×25 cm column with petroleum ether.

Lipase Column 3.5 g of the above-described immobilized lipase is packed in a 1.5×25 cm column with petroleum ether.

Substrate

Olive oil (Sigma 0-1500)/Decanoic acid (Merck) in a 2.5 to 1 w/w ratio stabilized with 0.1% BHT is used. The substrate is agitated in a reservoir at 60° C. and saturated with water. The incorporation of decanoic acid (D) in triolein (the major triglyceride in olive oil) to DOO-triglyceride is followed. The substrate is pumped downwards through the columns displacing the petroleum ether.

Analysis

The flowrate is adjusted to obtain approx. 23% DOO in the product stream, corresponding to 65% conversion of OOO+P to DOO+P. A 7–8 ml sample is weighed and the flow calculated in g/h.

For triglyceride (TG) composition analysis, 7 drops from the sample is dissolved in 4 ml heptane and put on a column with 12 g activated $Al_2O_3$ in heptane. Elution is done with 15 ml ether which is evaporated and the residue is redissolved in 1.5 ml heptane. With the HPLC done as described hereinafter in AF 206, DOO and DOD peaks appearing at 5.6 and 3.9 min. respectively.

The water content in the product stream is checked by Karl Fischer titration.

Column Performance

Samples were taken at 2 and 3 day intervals. Flowrate in g substrate/h was recalculated in g TG/h.g enzyme (F) as a measure of activity. Also the productivity in g TG/g enzyme (P) was calculated. The temperature was on average 60.3° C. with a standard deviation of 0.4° C.

Water content in the product dropped from 0.36% go 0.28% after 400 hours. The precolumn was then replaced and water dropped from 0.50 to 0.31% over the following 400 hours.

Data within a conversion of 23±1% DOO was used for a semi-log plot of flow vs. time. From this plot the initial activity is estimated to be $F_{init}$=1.94 g TG/h.g enzyme product catalyst with a half-life of 3100 h at 60° C. FIG. 1 is the plot of this test study.

The productivity assuming a run time of 2 half-lives should be 6.5 tons TG/kg of the enzyme product catalyst.

EXAMPLE 2

This Example illustrates the immobilization of lipase according to the invention on two similar phenolic adsorbent resins with or without high ionic strength during immobilization:

TABLE 2

| Macroporous Phenolic Adsorbent Resin | Particle Size 85% (μm) | Immobilization Without Salt | | | With 2 M Sodium Acetate | | |
|---|---|---|---|---|---|---|---|
| | | Yield (%) | Load (LU/mg) | Act. (BIU/g) | Yield (%) | Load (LU/mg) | Act. (BIU/g) |
| Duolite S-761 | 400–800 | 77 | 21 | 20 | 82 | 21 | 15 |
| Duolite ES-762 | 200–400 | 63 | 17 | 6.0 | 95 | 25 | 17 |

Determination of lipase batch interesterfication activity (BIU) according to NOVO method AF 206.

The principle is incorporation of free palmitic acid (P) in pure triolein (OOO), where the initial rate is calculated for this equilibrium fraction:

$$OOO + P \rightleftharpoons POO + O$$

$$POO + P \rightleftharpoons POP + P$$

PPP is not formed if the lipase (as, for example, *Mucor miehei* lipase) is 1,3 specific.

The value $P_{inc}$ is calculated at a given reaction time as the amount of palmitic acids in the 1 and 3 positions of triglyceride:

$$\% P_{inc} = \frac{\% POO + 2\% POP}{3}$$

An equimolar mixture of P and OOO is used and $P_{inc}$ will follow a conversion curve from 0 to approx. 21% at equilibrium.

This curve is fitted to an exponential model and the initial activity is calculated as 1 μmole of P incorporated in OOO per min. at 40° C. ~1 BIU.

678 μmole OOO and 678 μmole P in 12 ml of petroleum ether is mixed with 250 mg dry matter immobilized lipase, hydrated to 10% water. This mixture is shaken at 40° for 15 and/or 30 minutes, and the relative composition of OOO, POO and POP is measured by HPLC.

$$BIU/g = \frac{P_{inc,eq} \cdot \ln(P_{inc,eq}/(P_{inc,eq} - P_{inc})) \cdot M}{t \cdot w}$$

$P_{inc}$, eq is the equilibrium Pinc (mole fraction) ~0.222
$P_{inc}$ is calculated as described in mole fraction
M is the mole amount of OOO and P ~678 μmole
t is time in minutes
M is dry weight of catalyst (0.250 g)

Calculation of Conversion, Activity, Half-Life, and Productivity in Column Tests Degree of Conversion $$X = \frac{A - Ao}{A_{eq} - Ao}$$

A is % incorporated fatty acid in triglyceride (e.g., decanoic acid or palmitic acid in triolein)

Column or Flow Activity $$F = Fo \cdot \exp(-\ln 2 \cdot t/t_{\frac{1}{2}}) \; [g^{TG}/h \cdot g \, cat.]$$

Fo: initial activity; $t_{\frac{1}{2}}$ = half-life
Units of g triglyceride/hour.g catalyst is derived from the flow of substrate in g/hr by knowing the amount of triglyceride in the substrate and the amount of catalyst in the column.

Productivity $$P = \int_o^t F \cdot dt$$

I claim:

1. A method for production of an immobilized lipase preparation adapted for interesterification of fats, which comprises contacting an aqueous solution of *Mucor miehei* lipase with a particulate, macroporous, phenol-formaldehyde adsorbent resin having a particle size such that more than 90% of the resin particles have a size between 100 and 1000 μm, at a pH in range of 5–7 to bind said lipase to said resin to form said immobilized lipase whereby at least 75% of the lipase activity is removed from the aqueous lipase solution to form a spent aqueous solution, then separating the immobilized lipase from the spent aqueous solution and thereafter drying the separated immobilized lipase to a water content of between about 2 and 40%, the resulting preparation having an activity of at least 10 batch interesterification units (BIU) per gram dry basis, and at least 5000 lipase units (LU) per gram dry basis.

2. A method according to claim 1 further comprising water washing the immobilized lipase after separation from the spent aqueous lipase solution.

3. A method according to claim 1 wherein more than 90% of the particles of the macroporous adsorbent resin has a particle size between about 400 and about 800 μm.

4. A method according to claim 1 wherein the resin is contacted with said lipase in solution in an amount of between 5,000 and 20,000 LU/g dry basis adsorbent resin.

5. A method according to claim 1 wherein the lipase solution and the macroporous phenol-formaldehyde adsorbent resin are in contact for between 0.5 and 4 hours.

6. A method according to claim 1 wherein the separated immobilized lipase is dried to a water content between 5 and 20%.

7. The product of the method of claim 1.

8. A method for interesterification fats which comprises passing solvent free, melted fat(s) at temperature in the range of 50° C.-85° C. through a column of immobilized *Mucor miehei* lipase, said immobilized *Mucor miehei* lipase being lipase bound to particulate macroporous phenol-formaldehyde adsorbent resin having particle size such that more than 90% of the resin particles have a size between 100–1000 μm, said immobilized *Mucor miehei* lipase having an activity of at least 10 batch interesterification units (BIU) per gram dry basis and at least 5000 lipase units (LU) per gram dry basis and said immobilized *Mucor miehei* lipase having 2–20% water content when starting to pass the melted fat through the column of immobilized lipase.

9. A method according to claim 8 wherein the melted fat(s) contains free fatty acid therein.

* * * * *

UNITED STATES PATENT AND TRADEMARK OFFICE
CERTIFICATE OF CORRECTION

PATENT NO. : 4,798,793

DATED : January 17, 1989

INVENTOR(S) : Peter Eigtved

It is certified that error appears in the above-identified patent and that said Letters Patent is hereby corrected as shown below:

Col. 1, line 14: "Rhizopups" should read "Rhizopus".

Col. 2, line 6: "biotech-" should read "Biotech-".

Col. 3, line 56: "sustitution" should read "substitution".

Cols. 5 and 6 table 1: "um" should read "µm".

Col. 8, line 62: "go" should read "to".

Col. 9, line 46: "2% POP" should read "2 . % POP".

Col. 9, line 49: "21" should read "23".

Col. 9, line 64: "$P_{inc, eq}$" should be lowered a fraction of a mm.

Col. 9, line 65: "$P_{inc}$" should be lowered a fraction of a mm.

Col. 10, line 24: "$F_o$-exp" should read: $F_o$ . exp".

Col. 10, line 24: "F=Fo-exp (-In 2.t/t1/2)[$g^{TG}$/h.g cat.]
             should read
"F=Fo-exp (-In 2.t/t1/2)    [$g^{TG}$/h.g cat.]

Signed and Sealed this

Twenty-second Day of May, 1990

Attest:

HARRY F. MANBECK, JR.

Attesting Officer

Commissioner of Patents and Trademarks